United States Patent [19]

Kearns et al.

[11] Patent Number: 5,286,646
[45] Date of Patent: Feb. 15, 1994

[54] METHOD FOR MAMMALIAN CELL CULTURE

[75] Inventors: Michael J. Kearns, Seeshaupt; Michael J. Comer, Bernried; Ulrich Steegmans; Herbert Jungfer, both of Tutzing, all of Fed. Rep. of Germany

[73] Assignee: Boehringer Mannheim GmbH, Mannheim, Fed. Rep. of Germany

[21] Appl. No.: 763,867

[22] Filed: Sep. 20, 1991

Related U.S. Application Data

[63] Continuation of Ser. No. 409,959, Sep. 18, 1989, abandoned, which is a continuation of Ser. No. 934,662, Nov. 25, 1986, abandoned.

[30] Foreign Application Priority Data

Nov. 25, 1985 [DE] Fed. Rep. of Germany ....... 3541738

[51] Int. Cl.⁵ .............................................. C12N 5/06
[52] U.S. Cl. ........................... 435/240.24; 435/240.25; 435/240.2
[58] Field of Search ......... 435/240.1, 240.22, 240.242, 435/240.24, 240.25, 240.241, 286, 284, 311, 316, 813; 210/641, 649, 650

[56] References Cited

U.S. PATENT DOCUMENTS

| 3,769,176 | 10/1973 | Hise et al. ............................ 435/313 |
| 3,911,140 | 10/1975 | Osborne et al. ...................... 426/36 |
| 3,926,738 | 12/1975 | Nyiri et al. .......................... 435/290 |
| 4,075,100 | 2/1978 | Furuta et al. ..................... 210/500.23 |
| 4,391,912 | 7/1983 | Yoshida et al. ..................... 435/284 |
| 4,440,853 | 4/1984 | Michaels et al. .................... 435/284 |
| 4,559,299 | 12/1985 | Rotman ........................ 435/240.242 |
| 4,647,539 | 3/1987 | Bach .................................... 435/284 |
| 4,722,902 | 2/1988 | Harm et al. .......................... 435/311 |

FOREIGN PATENT DOCUMENTS 0039055 4/1981 Fed. Rep. of Germany .
0112155 12/1983 Fed. Rep. of Germany .
2238759 7/1973 France .

OTHER PUBLICATIONS

Feder et al., "The Large-Scale Cultivation of Mammalian Cells", *Scientific American*, Jan. 1993 pp. 36–43.
Gibco, BRL Catalogue & Reference Guide (1990) p. 96.
Gel Filtration: Theory & Practice, p. 27 (see table 7).
Cheryan et al. In Membrane Separations in Biotech. McGregor (eds) Marcel Dekker Inc. 1986 (see FIG. 15).
Gori, G. B., (1965) Chemostatic Dialyzed Cell Cultures, vol. 13, pp. 93–98.
Kearns, M. J., (1990) Bio/Technology, vol. 8, pp. 409–413.
Patent Abstracts of Japan, vol. 10, No. 67 (C-333) [2124] Mar. 15, 1986.
M. W. Glacken, "Mammalian Cell Culture: Engineering Principles and Scale-up" Trends in Biotechnology, vol. 1, No. 4, 1983, pp. 102–108.

*Primary Examiner*—Robert J. Warden
*Assistant Examiner*—Theresa A. Trembley
*Attorney, Agent, or Firm*—Felfe & Lynch

[57] ABSTRACT

The invention presents a method for the culturing of mammalian cells. This method involves the use of a bioreactor, which contains a sample of mammalian cells in a culture medium containing large molecules. Positioned inside the bioreactor is a semipermeable membrane which defines a space separated from the bioreactor by the semipermeable membrane. A nutrient medium flows through this separated space and, via virtue of the semipermeable nature of the separating membrane, nutrient pass therethrough into the culture medium, while cellular waste products pass into the separated space. The semipermeable membrane is selected so that the cells and large molecules, such as proteinaceous materials, cannot pass through the membrane, but remain in the bioreactor.

12 Claims, 2 Drawing Sheets

TIME [DAYS]

METHOD FOR MAMMALIAN CELL CULTURE

This application is a continuation of application Ser. No. 07/409,959, filed Sep. 18, 1989, which application is a continuation of application Ser. No. 934,662 filed Nov. 25, 1986, both now abandoned.

FIELD OF THE INVENTION

The present invention is concerned with a process and device for the biotechnological culturing of cells and especially for the multiplication of mammalian cells in vitro.

BACKGROUND AND PRIOR ART

In the scope of biotechnology, there are produced biological products, for example monoclonal antibodies, interferons, vaccines, plasminogen activators and the like, with the help of cells and especially of mammalian cells. However, the economics of such processes depend essentially upon the cells multiplying as much as possible and upon the highest possible concentration of the desired substance being produced in the interior of the cells. In order to achieve these objects, special requirements are demanded of the processes and devices used for the large scale culturing of cells. Thus, in particular, provision must be made for a sufficient supply of nutrients, as well as of gases, particularly oxygen. Waste products, i.e. cell metabolic products, which are not needed in the cell culture and which frequently inhibit growth of the cells, must be removed. All other environmental conditions, for example temperature and pH value, must also be as optimal as possible.

In an article entitled "Mammalian cell culture: engineering principles and scale-up" by M. W. Glacken et al. in the periodical "Trends in Biotechnology", pp. 102–108/1983, there are discussed these problems and a number of constructional principles for appropriate apparatus for the culturing of cells.

As can be seen from this article, it is necessary to differentiate between suspension cells and carrier-dependent cells. Whereas the suspension cells float freely in the cell culture medium and can grow therein, carrier-dependent cells, which are also called adherent cells, require a solid carrier in order to be able to survive and grow.

In this article, besides the above-mentioned problems, there are, in particular, discussed the problems of "up-scaling". Thus, it has been found that methods which function adequately on a laboratory scale are unsuitable for large-scale production.

Traditionally, mammalian cells, as well as bacterial cells, are primarily cultured as suspension cultures in bioreactors which are also called fermenters. The environmental conditions can be precisely controlled in such vessels. A stirring means moves the culture medium in the interior of the reactor and thus provides for a homogeneous distribution of the cells. A corresponding culture technique is also possible for adherent cells in that they are present on small carrier spheroids which are referred to as "micro-carriers". These float in the culture medium.

The supply of nutrients to the cells and the removal of waste materials takes place, in the case of suspension cultures in bioreactors, according to one of the following three processes:

In a batch operation, the reactor is operated discontinuously. At the beginning of a batch, the culture medium usually contains a serum, for example fetal calf serum (FCS), and the necessary nutrients, for example glucose, vitamins, amino acids and minerals. In operation, these are consumed so that the medium becomes more and more impoverished in nutrients. At the same time, the concentration of waste products increases which finally results in a prevention of the cell growth. The result of this is a course of cell density curve such as is shown in FIG. 1a of the accompanying drawings. The cell density achieves a maximum value of about $10^6$ cells/ml. and thereafter decreases again. Consequently, the culturing is discontinued when the maximum cell density is achieved. The contents of the reactor is then passed on for further working up. This process is unsatisfactory insofar as the environment of the cells changes continuously so that, during most of the time of the fermentation procedure, it is by no means optimal.

This could be improved by repeatedly refreshing the culture medium without thereby removing cells. However, for this purpose, a part of the culture medium must be repeatedly removed even though it has by no means been consumed. Such a process is extremely expensive because the known culture media are difficult to obtain and, consequently, are expensive.

Better in this regard is the so-called "feedbatch process" in which, during the fermentation procedure, fresh culture medium is not supplied in its totality but only the consumed nutrients are continuously supplied. However, in practice this process does not provide any substantial advantages because the increase of the waste materials leads to a characteristic course of the cell density during the culturing procedure similar to that in the case of the purely batch process.

The third process is the continuous process in a so-called chemostat or cytostat. Here, the environmental conditions can be uniformly adjusted so that the cells can grow optimally. However, the process is very laborious and expensive because culture medium must be continuously supplied and removed. Furthermore, in the case of this process too, there is not achieved a substantially higher cell density than in the case of the above-mentioned processes because cells are also continuously removed from the reactor with the running off of cell culture medium.

Regardless of which of the three described operational processes is chosen for the suspension cultures, the results are not satisfactory especially because the consumption of valuable culture medium is too high and because a higher maximum cell density is desirable. This latter criterion is of especial importance because present experience shows that the concentration of the desired products in the cells increases with increasing cell density. Therefore, an increase of the cell density leads to an overproportional increase of the yield of product.

In order to achieve a further improvement, new processes have been suggested.

The so-called "systems with artificial capillaries" consist essentially of a bundle of hollow dialysis fibres which are arranged in the interior of a hollow cylinder. They are especially recommended for the culturing of adherent cells. The cells are thereby applied to the outer side of the hollow fibres and are present in the intermediate spaces between the hollow fibres within the cylindrical housing. A culture medium flows through the inner side of the capillaries and air is supplied to the cells through the outer side of the housing. With such a process, there is achieved a comparatively uniform and economic supply of the nutrients to the cells. The cell density can also be slightly increased. Although the supply of nutrients is uniform, nevertheless it has been shown that the cells are supplied to a varying extent. This is especially due to the fact that they are positioned on the capillaries in several layers. The supply of oxygen is thereby also limited which can result in an increased production of waste products.

Such hollow fibre fermenters are described in European Patent Specifications Nos. 0,112,154 and 0,112,155. In the latter Specification, the system is varied insofar as the cells are pumped by means of a pump in circulation through the culturing module.

Hollow fibers, the walls of which consist of a membrane material, are also used in the cell culturing process described in published Japanese Patent Specification No. 60-207581. The hollow fibers are present in the culture medium in the inner chamber of a fermenter. The inside of the hollow fibers is connected with the outside of the fermenter via a single pipe which serves not only for the supply but also for the removal of liquids. With the help of a pump, waste materials of the cells are sucked off through this pipe through the wall of the hollow fibres or, in a cycle chronologically separate therefrom, sterilized water, which does not harm the cells, is introduced. Nutrients for cells can possibly also be added to this sterilized water. In operation, pumping into the culture liquid and sucking out therefrom is carried out alternatingly. This cycle is repeated continuously. In order to avoid the disadvantages of this discontinuous method of operation, there is preferably used an even number of hollow fibre bundles which are operated alternatingly, i.e. while sucking off from the culture medium through one half of the hollow fibre bundles, liquid is introduced through the other half of the fibre bundles. This process is comparatively laborious and involves the danger that the hollow fibres are damaged by the continuously alternating pressure loading from one side to the other.

Another novel technique involves the enclosure of the cells in spheroidal microbodies made of a semipermeable membrane material. This is indicated in the cited article as the sole new process for the culturing of suspension cells. It leads to an increase of the cell density in the small spheroidal bodies which, in turn, results in an increase of the product yield. The harvesting of the cells is simple because the spheroidal bodies settle out due to gravity, whereas individual cells must, as a rule, be centrifuged. These advantages are countered by the very high costs for the encapsulation of the cells. Furthermore, the supply of oxygen to the cells is limited which, in turn, reduces the success of the culturing.

DESCRIPTION OF THE INVENTION

Based upon this background, it is an object of the present invention to provide a simple and economic process and an appropriate device for culturing cells which makes possible an increased cell density and, consequently, an increased product yield.

Thus, according to the present invention, there is provided a process for culturing cells in which a cell culture in a reactor is kept in substantially homogeneous suspension under controlled environnental conditions, nutrients for the cells are introduced and cell waste products are removed, wherein there is used a nutrient medium separate from the culture medium, which nutrient medium flows in a cycle in a flow path separated from the culture medium by a semipermeable membrane, the membrane being such that it is permeable for the nutrients and the cell waste products but is impermeable for high molecular weight components of the culture medium, the culture medium with the cells is passed by on one side of the membrane and the nutrient medium containing the nutrients is passed by on the other side of the membrane so that nutrients from the nutrient medium pass through the membrane into the culture medium and waste materials pass from the culture medium into the nutrient medium.

The membrane is preferably arranged inside the reactor and the culture medium is preferably passed by it in such a manner that it is in the reactor chamber. The membrane is preferably in the form of hollow fibres through the inner space of which is pumped the nutrient medium.

The present invention also provides a device for culturing cells comprising a reactor, devices for controlling definite environmental conditions and stirring means for a culture medium present in the inner chamber thereof, wherein a semipermeable membrane dialyser is provided which separates a first chamber from a second chamber, said first chamber being connected to a reservoir for nutrient medium via an inlet pipe and a return pipe and said second chamber being connected with the inner chamber of the reactor, and having a device for introducing nutrient medium from the nutrient medium reservoir via an inlet pipe to the first chamber and for returning from the first chamber via the return pipe to the reservoir and for passing the culture medium on the side of the membrane lying opposite the first chamber.

The membrane is preferably in the form of hollow fibres and is preferably arranged in the reactor, the second chamber being a part of the inner chamber of the reactor. The exchanger surface of the dialysator is preferably at least 0.01 $m^2$/ liter and at most 0.3 $m^2$/ liter of culture medium and more preferably at least 0.03 $m^2$/ liter and at most 0.2 $m^2$/ liter of culture medium. Furthermore, the stirring means preferably comprises at least one marine impeller.

The present invention is based upon the bioreactor, the inner chamber of which contains the cells. It is especially suitable for suspension cells but can also be used for adherent cells, especially when these are present on micro-carriers such as is described in the cited article. In the reactor, the cells are kept in substantially homogeneous suspension with the help of a stirring device. The environmental conditions, i.e. especially the temperature, the oxygen partial pressure and the pH value, are controlled with the processes known for bioreactors and are kept constant in the optimum range.

An important difference with regard to the known processes is, in the case of the present invention, the fact that the nutrients are supplied to the cells and the waste products are removed from the cells. This takes place with the help of a semipermeable membrane which separates two chambers from one another. To one side of the membrane is supplied the culture medium from the inner chamber of the reactor. Besides the cells, it contains, in particular, the proteinaceous substances always contained in the known culture media, especially the above-mentioned fetal calf serum. Separate from the culture medium is a nutrient medium which only contains the relatively low molecular weight nutrients which are continuously utilized by the cells.

A semipermeable membrane is a separating wall through which some molecules can diffuse whereas other molecules are held back. For the present invention, the permeability of the membrane must be such that it is permeable for the relatively low molecular weight nutrients of the cells, as well as for their waste products, whereas it is impermeable for the higher molecular weight components of the culture medium. Consequently, the membrane firmly holds the high molecular weight and especially the valuable components of the culture medium. During the culturing procedure, they are practically not consumed so that they do not have to be introduced. The low molecular weight nutrients, on the other hand, can pass through the membrane so that on both sides of the membrane substantially the same concentration of these materials prevails. The similar thing also applies to the waste products of the cells which pass from the culture medium through the membrane into the nutrient medium.

Both media are kept in movement in such a manner that they continuously flow past the side of the membrane in question. In this way, on the one hand, there is continuously maintained on the nutrient medium side of the membrane a sufficiently high nutrient concentration and a sufficiently low waste material concentration and, on the other hand, the culture medium as a whole is so substantially homogeneous that substantially optimum growth conditions for the cells prevail overall. More particularly, the concentration of the nutrients in the nutrient medium, the rate of flow with which the nutrient medium flows past the dialysis membrane and the exchange surface of the dialysis membrane, as well as the rate of flow with which the culture medium flows past the membrane, must be so adapted to one another that, in the stationary state, the concentration of the nutrients in the culture medium is optimized and that the concentration of the waste materials in the culture medium is so small that the growth of the cells is not substantially disturbed.

Surprisingly, we have found that, in this way, with the help of a dialysis membrane, not only its immediate proximity in the dialyser but the whole inner chamber of a bioreactor can be supplied extraordinarily well with nutrients and that the waste products can be kept at such a low concentration that they scarcely disturb the growth. Over all, there is thus achieved, as is described in more detail hereinafter, cell densities and product yields which are far superior to those of the conventional suspension cultures. Nevertheless, the process is simple and very well suited for large scale production.

The semipermeable membrane can be formed as a flat surface which separates two appropriate chambers. It can also be made in the form of a tube or a plate dialyser can be used. Membrane hollow fibres are especially preferably used. The nutrient medium thereby preferably flows in the interior of the hollow fibres, whereas the culture medium flows over the outer side of the hollow fibres.

A first embodiment of the present invention, which is especially suitable for the equipment of bioreactors already available, provides that the membrane is arranged outside of the bioreactor. The membrane is present in a housing in which it separates two chambers. This unit is hereinafter called a dialyser. The nutrient medium side of the membrane, which in the case of a hollow fibre dialyser is preferably the interior of the hollow fibres, is thereby connected with a supply tank for the nutrient solution. By means of a pump, the nutrient solution is pumped in circulation through the dialyser and back into the supply container. In a second circulation, the culture medium is removed from the bioreactor, also pumped through the dialyser on the culture medium side of the membrane and back again into the bioreactor.

In comparison therewith, a version is especially preferred in which the membrane is arranged in the bioreactor. In the case of membrane hollow fibres, this can be achieved in such a way that the hollow fibre bundle, which is provided on both ends with appropriate connection heads, is freely arranged in the bioreactor. In this case, the culture medium is passed along the semipermeable membrane by means of a stirrer device present in the bioreactor. The stirring device is preferably so adjusted that a rotation of the culture medium is achieved with a high exchange of the medium in the region of the membrane.

Surprisingly, in the case of this simple process, there is achieved a sufficiently good exchange between nutrient medium and culture medium. Due to the open arrangement of the membrane in the interior of the bioreactor, there are no narrow canals in which there could result a stoppage due to the cells or the proteinaceous components of the medium.

Instead of the hollow fibre dialyser, there can also be used some other form of membrane, even though this is less preferred, arranged in appropriate manner in the interior of the bioreactor The present invention provides, in particular, the following advantages: the cell density is approximately ten times greater than in the case of the conventional suspension culture processes in bioreactors. It is achieved in about 8 days and approaches asymptotically a maximum value (see FIG. 1c of the accompanying drawings), i.e. a drop of the cell density does not occur after achievement of the maximum. Consequently, it is not necessary continuously to supervise the culturing procedure in order to ascertain the optimal point of time for harvesting the cells. The concentrations of the nutrients and of the toxic waste products are almost constant and can very readily be optimized.

The product yields are, especially because of the high cell density, up to 30 times as high as in the case of the conventional processes.

Very much less culture medium is utilized. Consequently, there is a large saving, especially of serum. This is, in part, also associated with the high cell density because the same amount of culture medium suffices in the case of the process according to the present invention for the production of a very much greater amount of cells and cell products. In addition, as already mentioned, the serum, in contradistinction to the mentioned perfusion process, does not have to be renewed or supplemented during the processing of a batch, only the substantially more economic nutrients being consumed.

In comparison with the above-mentioned new processes (cell culture on synthetic capillaries, encapsulation in membrane capsules), which in part also achieve a really high cell density, the present invention is, in particular, superior in that in the bioreactor the environmental conditions can be achieved and regulated very exactly. Thus, for example, the pH value and the oxygen partial pressure can be continuously measured and appropriately corrected. Because of the homogeneity of the suspension in the bioreactor, the values are overall substantially the same. Furthermore, the process according to the present invention is extremely simple. The investment costs are comparatively small, the possibilities of upscaling are very good and no laborious additional process steps, such as in the case of encapsulation, are required.

DESCRIPTION OF FIGURES AND OF PREFERRED EMBODIMENTS

The present invention and the advantages which are achieved therewith are explained in more detail in the following on the basis of embodimental examples which are illustrated in FIGS. 2 and 3. In the accompanying drawings.

Figure 2:
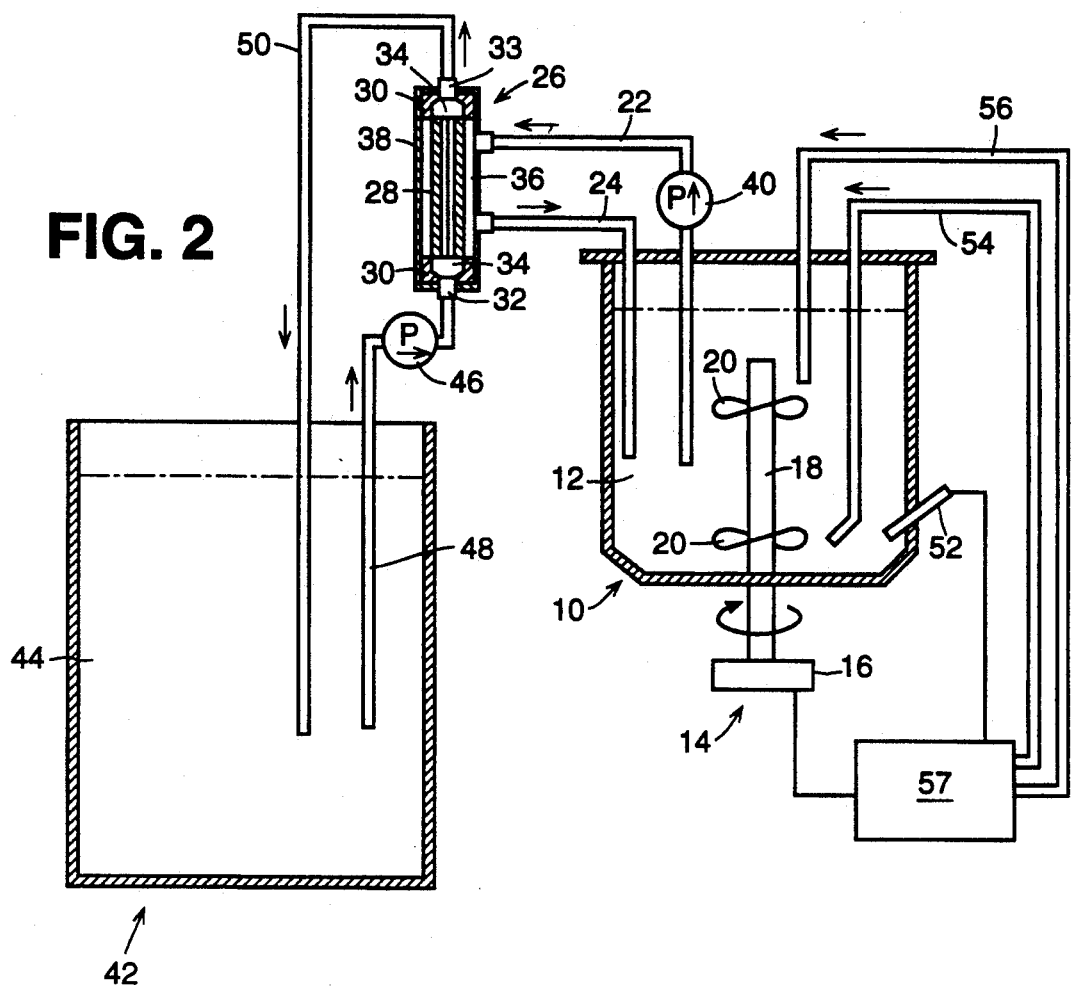
FIG. 2 is a schematic illustration of a device according to the present invention in which a dialyser with the membrane is present outside of the bioreactor.

The bioreactor 10 illustrated in FIG. 2 is filled with a culture medium 12. This culture medium contains high molecular weight proteinaceous components, especially sera, for example fetal calf serum. A stirring device 14 is provided for the homogenization of the culture medium. This consists essentially of a motor 16, an axle 18 passing through the wall of the reactor and stirring elements 20 fixed thereon. The stirring elements 20 are preferably made like propellers (so-called propeller impellers). Such a form of stirring elements, which are characterized by rounded boundary lines and a slope of the angle of incidence of the stirrer blades increasing continuously from outside towards the inside, has proved to be especially preferable in order to achieve the degree of homogenization of the culture medium necessary for the present invention without damaging the extremely sensitive cells of the culture.

The inner chamber of the bioreactor 10 is connected via pipes 22 and 24 with a dialyser 26. The schematic illustration shows a hollow fibre dialyser which is preferably used. It is constructed in a manner similar to that which is usual in the case of dialysers for blood dialysis (so-called artificial kidneys). In the drawing, on both ends of the dialyser there can be seen a connection head 30. The hollow fibres 28 run between the connection heads. The connection heads are so constructed that the open ends of the hollow fibres are in hydraulic connection with the connection pipes 32 and 33 for the dialysate. Thus, the inner spaces of the hollow fibres and the connecting canals up to the connection pipes form, connected with one another, a first chamber 34 which can be called the dialysate chamber. This is completely separate from a second chamber 36 formed on the outer side of the hollow fibres through which chamber 36 the culture medium flows. It is bounded essentially by the preferably substantially cylindrical wall 38 of the dialyser 26 and by the outer surfaces of the hollow fibres 28. Further details as to how such a dialyser can, for example, be constructed, are given in European Patent Specification No. 0,039,055, which is concerned with a blood dialyser.

The culture medium is introduced by means of a pump 40 via the pipe 22 to the described second chamber 36 of the dialyser, flows along on the side of the dialysis membrane associated with the culture medium and flows back via the pipe 24 into the bioreactor 10.

Nutrient medium 44 is present in a nutrient medium tank 42. This medium consists of an appropriate carrier liquid and various low molecular weight components which are needed for the nutrition of the cells, which include glucose, vitamins, amino acids and minerals. By means of a pump 46, nutrient medium is introduced via the pipe 48 into the dialysis chamber 34 of the dialyser 26. It there flows through the hollow fibers 28 and flows back through the pipe 50 into the nutrient medium tank 42.

The nutrient medium 44 in the nutrient medium tank 42 is renewed or supplemented sufficiently frequently that the desired nutrient concentration on the nutrient medium side of the dialysis membrane is maintained. This can be achieved either in that the nutrient medium tank 42 is so large that the change of the nutrient concentration taking place in the course of a culturing procedure does not disturb or the culture medium can be renewed during a culturing procedure. A continuous introduction of nutrients, which maintains the concentration in the nutrient medium tank 42, can also be advantageous.

Instead of the illustrated manner of operation, a hollow fiber dialyser can also h=introduced into the two circulations for the nutrient medium, on the one hand, and the culture medium, on the other hand, in such a manner that the culture medium flows through the interior of the hollow fibers, whereas the nutrient medium flows over their outer side. However, this is less preferred because there is a danger of a stoppage of the hollow fibres by the cells.

Instead of a hollow fibre dialyser, there can also be used another known type of dialyser. In any case, it is important that the first chamber of the dialyser for the nutrient medium and the second chamber of the dialyser for the culture medium, which, of course, must be completely separate from one another, are so constructed that an exchange is only possible via the dialysis membrane so that the necessary exchange surface is ensured For the process according to the present invention, the exchange surface is preferably from 0.01 $m^2$/liter of culture medium to 0.03 $m^2$liter of culture medium and is especially preferably from 0.03 $m^2$ to 0.2 $m^2$/liter of culture medium. Furthermore, the course of flow, especially in the second chamber 36 through which the culture medium flows, must be such that the cells can never cause a blockage and the culture medium can flow through the chamber as smoothsurfacedly as possible.

The dialysis membranes can be produced from a large number of materials known for such purpose. In particular, there are known cellulose acetate, acrylic copolymers and polysulphone fibers. Fibers made from cuprammonium rayon are especially preferred for the present invention. It is important that the membrane is permeable for the low molecular weight nutrients but is impermeable for the high molecular weight proteinaceous substances of the culture medium. In practice, there has proved to be useful a membrane with a molecular cut-off at a molecular weight of about 10,000 daltons but a membrane with a molecular cut-off of 100,000 daltons can also be preferred in individual cases.

The bioreactor is provided with devices 57 for monitoring and maintaining constant the environmental conditions for the cells in the culture medium 12. In particular, there are provided sensors for the pH value, the oxygen partial pressure and the temperature in the bioreactor 10. In the drawing, they are indicated in their totality by the reference numeral 52. The devices 57 for monitoring and maintaining constant the environmental conditions also include a pipe 54 for the introduction of gases through which, in particular, oxygen is introduced and a pipe 56 for the introduction of acid and/or alkali with the help of which the pH value is controlled. These devices 57 are generally known for suspension cultures in bioreactors. However, the present invention is especially characterized in that it not only makes possible, as in the case of the known bioreactors, a very precise control of the temperature, of the oxygen partial pressure and of the pH value but also that, at the same time, the concentrations of the nutrients and of the waste products of the cells can be well controlled and kept substantially constant in a range which makes possible an optimum cell growth.

Figure 3:
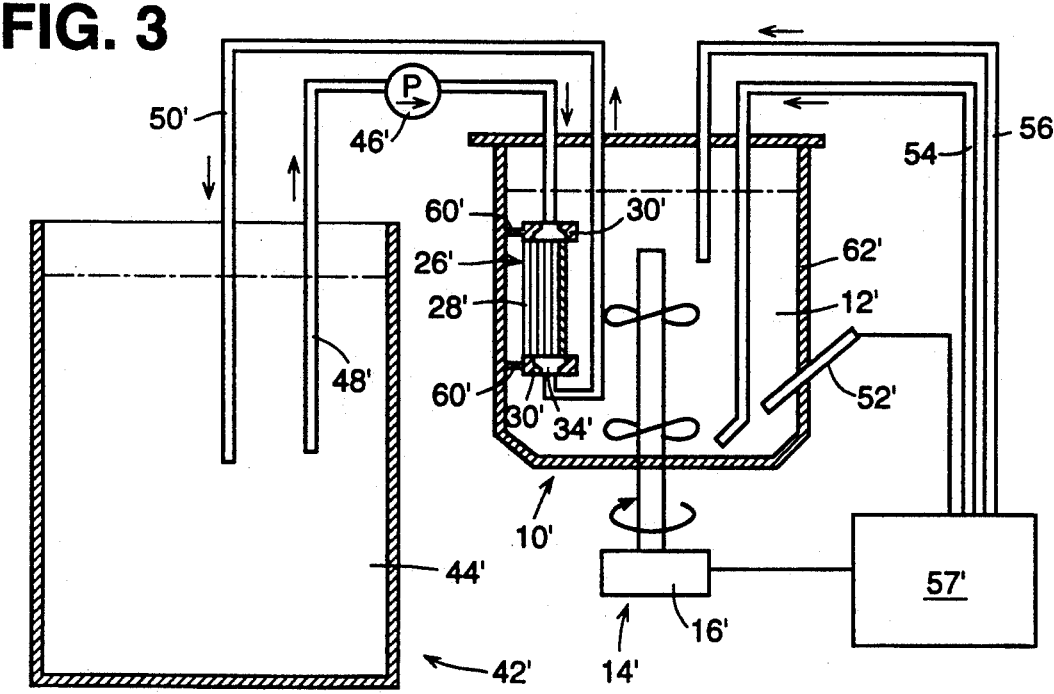
FIG. 3 is a schematic illustration of a device according to the present invention in which the membrane is present in the bioreactor.

FIG. 3 shows an especially preferred embodiment of a device according to the present invention which, in comparison with the embodiment illustrated in FIG. 2, differs in that the semipermeable membrane is arranged in the bioreactor. In this Figure, the corresponding parts have the same reference numerals as in FIG. 2 but with an additional stroke.

In the case of this embodiment of the present invention, membrane hollow fibres 28' are used which are freely stretched between the two connection heads 30' within the bioreactor 10' and form a dialyser 26', the hollow fibre bundles of which are not surrounded by a housing wall. The connection heads 30' are secured by means of an appropriate holding means 60' to wall 62' of the bioreactor 10' As in the case of the embodiment according to FIG. 2, here too the pipe 48', the dialysate chamber 34' (which is formed by the hollow chambers in the connection heads 30' and the inner chambers of the hollow fibres 28') and the pipe 50' form a closed circulation for the nutrient medium 44'. An exchange between the nutrient medium 44' and the culture medium 12' in the bioreactor 10' is only possible via the walls of the hollow fibres 28' acting as dialysis membrane.

In the case of this embodiment, the culture medium is not introduced in a closed circulation to the second chamber of the dialyser provided for the culture medium but rather is rotated in the bioreactor in such a manner that in the region of the surroundings of the dialyser 26' it is in constant movement and is passed past the dialysis membrane. Thus, in this case, the second chamber of the dialyser is not a closed chamber but rather forms a non-bounded part of the inner chamber of the bioreactor 10'. Surprisingly, such a simple construction gives an excellent result. On the one hand, the exchange of the nutrients and of the waste materials via the dialysis membrane is so good that the concentration thereof in the bioreactor can be kept substantially constant in the optimum range. On the other hand, the problems possibly observed with an embodiment according to FIG. 2 of a stoppage of the pipes for the culture medium can be dependably avoided in the case of this embodiment.

The device according to the present invention is preferably operated in the following manner:

The culture medium is placed, together with a starting culture of the cells, into the bioreactor and this is closed. Thereafter, the pumps and stirring devices, as well as the devices for controlling the environmental conditions, are set into operation so that the culturing procedure can take place. During the culturing procedure, the plant must merely be monitored and care taken that the nutrient concentration is maintained in the above-described manner.

Figure 1A:
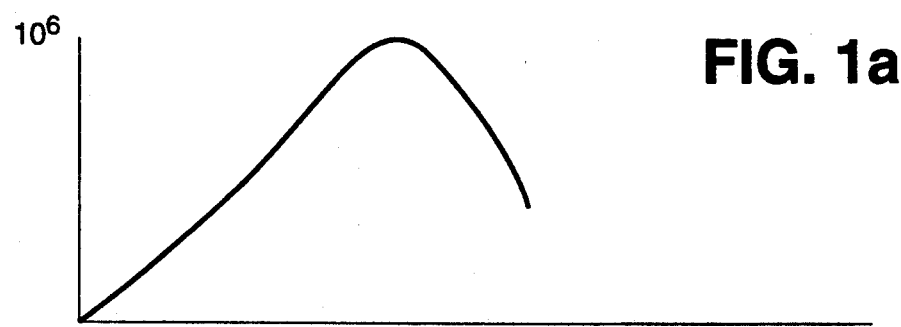
FIG. 1a to FIG. 1c show the chronological development of cell density in various suspension cell cultures in the bioreactor on about the same scale, namely, FIG. 1a for a simple batch operation, FIG. 1b for operation with a continuously supplied culture medium (chemostat) and FIG. 1c for the process according to the present invention.
Figure 1B:
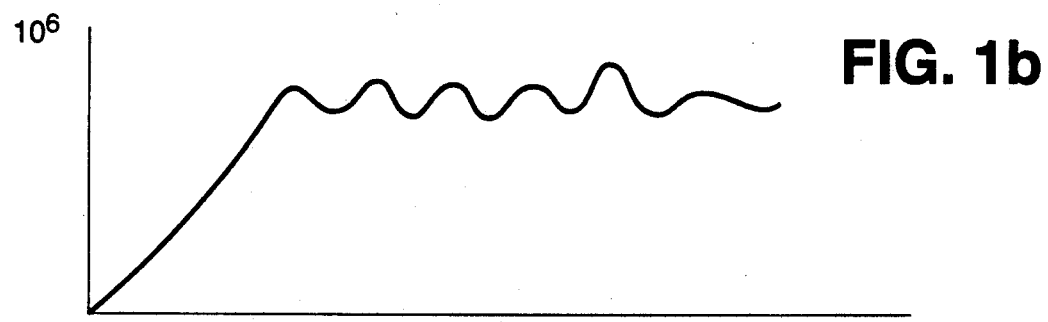
Figure 1C:
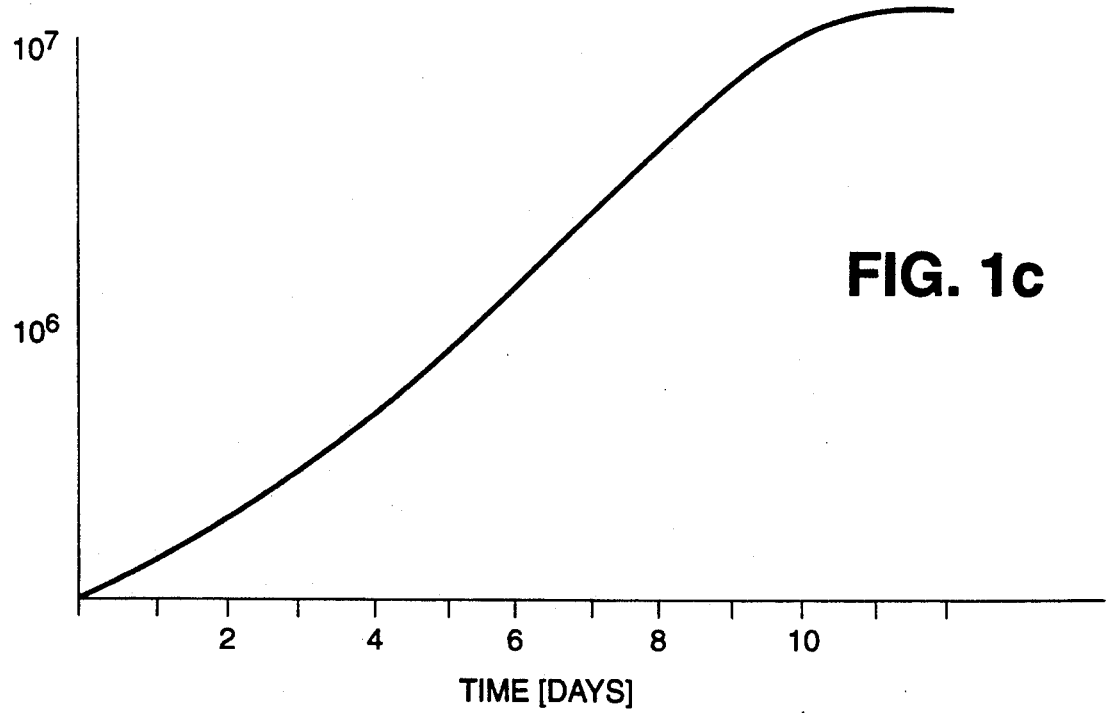

During the operation, on the membrane of the dialyser there flows past, on the one hand, the nutrient medium and, on the other hand, the culture medium with controlled speed. The low molecular weight components of both media are exchanged via the dialysis membrane. The speed with which, on the one hand, nutrients pass over from the nutrient medium into the culture medium and, on the other hand, the waste products of the cells from the culture medium into the nutrient medium is, as is known, dependent upon the concentrations of the materials in question on both sides of the membrane and upon the membrane surface. The material concentrations on both sides depend, in turn, upon the starting concentrations in the reservoirs, thus, on the one hand, in the bioreactor and, on the other hand, in the nutrient medium store, as well as upon the speed with which the media flow past the membrane. Because of these known relationships, it is possible so to adjust the individual parameters that during the culturing the nutrient concentration and the waste material concentration in the culture medium in the bioreactor lie in the optimum range. After a running-in phase, in the case of appropriate adjustment, a stationary state is obtained in which not only the nutrient concentration but also the waste material concentration are substantially constant Since, as mentioned, the other environmental conditions are kept constant in the optimum range, the cell culture grows in the manner illustrated in FIG. 1c until the cell density has achieved a maximum value which is much higher than in the case of the known culturing processes. This value remains substantially constant. When it is achieved, the bioreactor can be opened and the cell culture harvested in known manner.

In the following Table, there are given the results which can be achieved with the process according to the present invention and an appropriate device and compared with the results of the cell culturing in a bioreactor suspension culture which was operated in a batch operation without a dialyser. The results are given for four different hybridoma cell lines. It can be seen from the Table that, depending upon the cell type, there is achieved an improvement of the maximum cell density of between about a factor of 6 and a factor of 12. The maximum antibody concentration in the culture is even more considerably greater improved, namely, by a factor of 12 up to a factor of more than 30.

TABLE

| cell line | origin | maximum cell density (number per ml.) | | maximum antibody concentration ($\mu$g./ml.) | |
| --- | --- | --- | --- | --- | --- |
| | | known batch bioreactor culture | bioreactor culture according to invention | known batch bioreactor culture | bioreactor culture according to invention |
| 1 | mouse | $10^6$ | $6 \times 10^6$ | 20 | 300 |
| 2 | human | $1.5 \times 10^6$ | $2 \times 10^7$ | 0.3 | 11 |
| 3 | human | $1.5 \times 10^6$ | $10^7$ | 0.5 | 13 |
| 4 | human | $1.5 \times 10^6$ | $10^7$ | 0.8 | 10 |

While there have been described what are at present considered to be the preferred embodiments of this invention, it will be obvious to one skilled in the art that various changes and modifications may be made therein without departing from the invention, and it is, therefore, aimed to cover all such changes and modifications as fall within the spirit and scope of the invention.

We claim:

1. In a process for culturing mammalian cells for production of biological products in a batch fermenter having means for monitoring and controlling the environmental conditions of the cells and wherein the cells are in homogeneous suspension the improvement comprising
   a) maintaining and culturing mammalian cells in a homogeneous suspension to a final concentration of more than $1.5 \times 10^6$/ml in a batch fermenter which contains a cell culture medium containing high molecular weight proteinaceous material required for mammalian cell proliferation,
   b) providing a nutrient medium, without transporting any high molecular weight proteinaceous material therewith, to the cells while simultaneously maintaining the high molecular weight proteinaceous materials within the cell culture medium in situ by means of a device inside said batch fermenter being in contact with the cell culture medium, said device containing a multiplicity of hollow fibers which multiplicity of hollow fibers are freely immersed in the cell culture medium contained in the batch fermenter said multiplicity of hollow fibers having an outer semipermeable membrane and an inner hollow space wherein the outer semipermeable membranes have an exchange surface of less than $0.3 m^2$ per liter of cell culture medium, wherein the cell culture medium is in revolving motion to continuously flow past the multiplicity of hollow fibers without damage to the cells and wherein the inner hollow space of the multiplicity of hollow fibers is connected to a source of the nutrient medium and the nutrient medium passes to the cells and cell waste from the cell culture medium passes to the nutrient medium to minimize the presence of cell waste in the cell culture medium via the outer semipermeable membrane of the hollow fiber, wherein the high molecular weight proteinaceous material of the cell culture medium is maintained in situ and cannot pass the semipermeable membrane of the hollow fibers.

2. Process of claim 1 wherein said outer semipermeable membrane has an exchange surface of from 0.01 $m^2$/liter to less than 0.3 $m^2$/liter of cell culture medium.

3. Method of claim 2 wherein said outer semipermeable membrane has an exchange surface of from 0.03 $m^2$/liter to 0.2$m^2$ liter of cell culture medium.

4. Process of claim 1 wherein said mammalian cells are kept in revolving motion by a stirring means which comprises at least one marine impeller.

5. Process of claim 1, wherein said mammalian cells are suspension cells.

6. Process of claim 1, wherein said mammalian cells are adherent cells on micro-carriers.

7. Process of claim 1, wherein said outer semipermeable membrane comprises cuprammonium rayon fabric.

8. Process of claim 1, wherein said outer semipermeable membrane comprises cellulose acetate.

9. Process of claim 1, wherein said outer semipermeable membrane comprises an acrylic copolymer.

10. Process of claim 1, wherein said outer semipermeable membrane comprises a polysulphone fabric.

11. Process of claim 1, wherein said outer semipermeable permits passage of molecules with molecular weight up to 100,000 daltons.

12. Process of claim 1, wherein said outer semipermeable permits passage of molecules with molecular weight up to 10,000 daltons.

* * * * *